Figure 1:
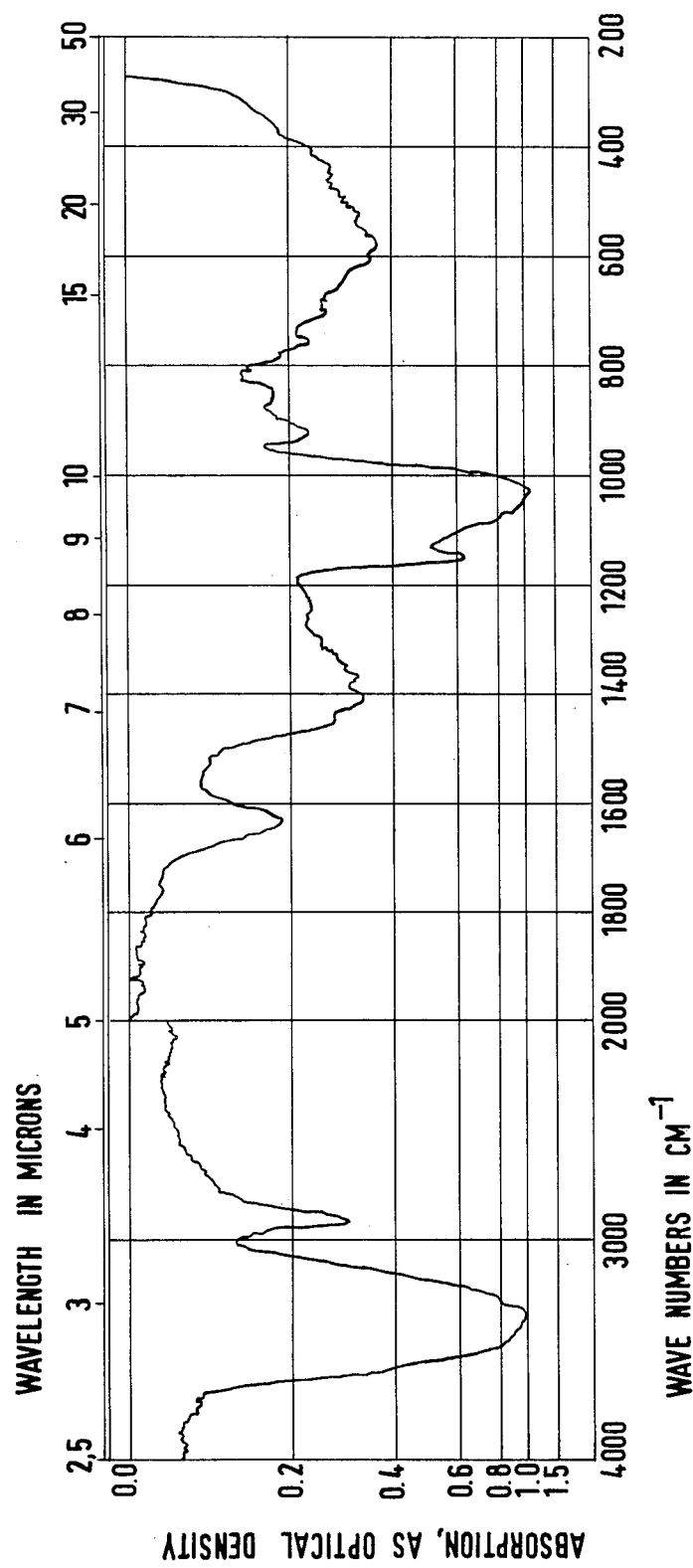

United States Patent [19]

Belloc et al.

[11] 4,271,067

[45] Jun. 2, 1981

[54] GLYCOPEPTIDE

[75] Inventors: Andre Belloc, Vanves; Jean Florent, Boulogne-Billancourt; Jean Lunel, Paris; Denise Mancy, Charenton; Jean-Claude Palla, Thiais, all of France

[73] Assignee: Rhone-Poulenc Industries, Paris, France

[21] Appl. No.: 760,978

[22] Filed: Jan. 21, 1977

[30] Foreign Application Priority Data

Jan. 22, 1976 [FR] France .................. 76 01647

[51] Int. Cl.$^3$ .................. C12P 21/00; A61K 37/00
[52] U.S. Cl. .................. 260/112 R; 435/68; 435/886; 435/803; 424/177
[58] Field of Search .................. 195/80 R; 260/112 R; 435/68; 424/177

[56] References Cited

U.S. PATENT DOCUMENTS

| | | | |
|---|---|---|---|
| 3,806,421 | 4/1974 | Ueda et al. | 195/80 R |
| 3,876,766 | 4/1975 | Frommer et al. | 195/80 R X |

*Primary Examiner*—Lionel M. Shapiro
*Attorney, Agent, or Firm*—Stevens, Davis, Miller & Mosher

[57] ABSTRACT

The glycopeptide 31,177 RP is prepared by cultivating under aerobic conditions in an aqueous nutrient medium *Streptomyces calidus* DS 26,320 (NRRL 8141), a hitherto unknown microorganism. 31,177 RP is of interest as an inhibitor of glyco-hydrolases, e.g. the amylases, the maltases or the saccharases, particularly those of the digestive tract.

11 Claims, 4 Drawing Figures

GLYCOPEPTIDE

This invention relates to a glycopeptide, hereinafter denoted by the number 31,177 RP, to a process for its preparation and to pharmaceutical compositions containing it.

31,177 RP is of particular interest as an inhibitor of glyco-hydrolases such as the amylases, the maltases or the saccharases and particularly those of the digestive tract.

The glycopeptide 31,177 RP may be obtained by culture, under appropriate conditions, of a microorganism of the genus Streptomyces, identified more completely hereinafter and denoted by the name *Streptomyces calidus* DS 26,320. A specimen of the microorganism has been deposited with the United States Department of Agriculture, Northern Regional Research Laboratory at Peoria, Illinois, United States of America, and has been given the number NRRl 8141. A sample of the microorganism can be obtained from the aforementioned Research Laboratory.

The glycopeptide 31, 177 RP according to the invention is characterised by the following physico-chemical properties:

it is soluble to the extent of more than 1,000 g/l in water; its solubility decreases rapidly in aqueous-alcoholic and aqueous-acetone mixtures and drops to less than 0.1 g/l in anhydrous alcohols, acetone, hexane, ethyl acetate, diethyl ether and chlorinated solvents;

analysis of the products of acid hydrolysis shows principally lysine and glucose;

it contains carbon, hydrogen, oxygen, nitrogen and sulphur, the relative proportions being approximately: C=46.2% H=6.05% O=46.11% N=1.44% S=0.20%;

its molecular weight is between 10,000 and 20,000; its optical rotation (c=0.4, water) is:

$[\alpha]_D^{20} = +149.5 \pm 2.5°$
$[\alpha]_{436}^{20} = +295 \pm 4.0°$
$[\alpha]_{365}^{20} = +448 \pm 5.5°$ it does not exhibit a characteristic absorption in the ultraviolet spectrum between 220 and 400 nm;

its infra-red spectrum (determined on tablets of a mixture with KBr) is shown in FIG. I of the accompanying drawings, in which the abscissae give the wavelengths expressed in microns (upper scale) and the wave numbers in cm$^{-1}$ (lower scale), and the ordinate gives the optical density.

The principal infra-red absorption bands of 31,177 RP, expressed as wave numbers (cm$^{-1}$), are given in Table I which follows:

TABLE I

| | | | |
|---|---|---|---|
| 3470 sh | 2540 sh | 1335 sh | 760 m |
| 3400 sh | 2350 vw (CO$_2$) | 1305 sh | 720 sh |
| 3350 vs | 2100 vw | 1240 w | 700 m |
| 3270 sh | 1985 vw | 1160 s | 640 sh |
| 3100 sh | 1945 vw | 1100 sh | 610 sh |
| 3050 sh | 1900 vw | 1075 sh | 580 m |
| 3000 sh | 1850 vw | 1030 vs | 525 w |
| 2980 sh | 1760 vw | 935 sh | 440 sh |
| 2930 s | 1630 m | 920 m | 410 sh |
| 2900 sh | 1450 sh | 850 m | 370 sh |
| 2830 sh | 1410 s | 785 sh | |

TABLE I-continued

| | | |
|---|---|---|
| 2780 sh | 1370 w | 770 sh | vs = very strong
s = strong
m = medium
w = weak
vw = very weak
sh = shoulder 31,177 RP is further characterised by the following physico-chemical properties:

it is a white powder after lyophilisation;

it gives certain colour reactions of sugars [either directly (reaction with 3,5-dinitrosalicyclic acid), or after acid hydrolysis (reaction with 3,5-dinitrosalicylic acid, with anisaldehyde, with naphthoresorcinol, with aniline phthalate and with Somogyi-Nelson reagent)]. Conversely, the peptide determination by means of the Folin-Ciocalten reagent proves negative when carried out on 31,177 RP, but as indicated above analysis after acid hydrolysis shows the presence of lysine;

it is strongly retarded on porous gels of cross-linked acrylamide and of crosslinked dextran, which prevents any estimation of its molecular weight by their use;

according to its behaviour in ultrafiltration with membranes of controlled porosity, its molecular weight is between 10,000 and 20,000;

hydrolysis with normal sulphuric acid at 95° C. for 2 hours 30 minutes gives lysine only, identified by the Technicon auto-analyser, whilst after silylation of the hydrolysate and gas phase chromatography, it gives only monosaccharides consisting essentially of glucose.

31,177 RP is a very powerful inhibitor of pancreatic α-amylase, reduces and retards hyperglycaemia and hyperinsulinaemia following the ingestion of starch, and also possesses a noteworthy anti-saccharase activity and anti-maltase activity. Its toxicity is very slight.

Anti-enzymatic activity

The inhibitory activity displayed towards pancreatic α-amylase, towards maltase and towards saccharase was determined in vitro as follows:

Inhibitory activity on amylase

The amylase activity is determined in accordance with the method of G. Noelting and P. Bernfeld [Helv. Chim. Acta 31, 286 (1948)] in the presence and in the absence of the inhibitor to be determined. The activity is evaluated in international units. One unit of amylase is the amount of enzyme which liberates one microequivalent of reducing group, expressed as maltose, per minute, during the hydrolysis of the α-1-4-glycoside bonds of starch. The reducing groups react with 3,5-dinitrosalicyclic acid at the boil, causing a colouration to appear, which is measured at 540 mμ. With sufficiently low amounts of enzyme, linear kinetics lasting for several minutes and passng through the origin are obtained. A reference curve is drawn up with the aid of maltose.

The inhibitory activity is expressed in inhibitor units (I.U.). The amylase inhibitor unit is the amount of product which inhibits 50% of the activity corresponding to 2 units of amylase. Mixtures consisting of 0.5 ml of an enzyme solution containing 4 units of amylase per milliliter and 0.5 ml of an aqueous solution of inhibitor containing, respectively, 0, 0.100, 0.200, 0.300 and 0.400 µg/ml of 31,177 RP are produced. The mixtures are prepared at 35° C. and kept at this temperature for 15 minutes. The enzymatic activity of each of the mixtures is then measured in accordance with the technique described above. From the curve obtained by plotting the units of amylase activity as abscissae and the amount of inhibitor in µg/ml as ordinates, the 50% inhibitory concentration is deduced ($IC_{50}=0.106$ µg/ml of 31,177 RO). The $IC_{50}$ is then converted to inhibitory units per milligram of inhibitor (9,430 I.U./mg of 31,177 RP).

Alternatively, the concentration which makes it possible to reduce by 50% the action of pancreatic α-amylase on soluble starch, determined in accordance with the method recommended by the International Pharmaceutical Federation, J. Mond. Pharm. 3, 337 (1968), is 0.015 mg/l.

Inhibitory activity on saccharase

One saccharase inhibitor unit (SIU) is defined as the amount of inhibitor necessary to inhibit, by 50%, two saccharase units. One saccharase unit (SU) is the amount of enzyme which in one minute, under the experimental conditions given below, produces the scission of one micromole of sucrose into α-glucose and β-fructose. The α-glucose is determined after mutarotation to β-glucose, by the glucose-oxidase and o-dianisidine-peroxidase system, in accordance with the method described by A. Dahlquist [Methods in Enzymology 8, S. P. Colowick, N. O. Kaplan, p. 584, Acad. Press (1963) and Anal. Biochem. 7, 18 (1964)].

In order to carry out the measurement of the anti-saccharase activity, 0.14 ml portions of inhibitor solution, in a 0.1 M sodium maleate buffer of pH=6.0 (containing 0–400 mg/l of 31,177 RP) is added to 0.06 ml of saccharase suspension (0.165 SU/ml of saccharase extract from the small intestine of a rat, prepared in accordance with the method described by A. Dahlquist [Methods in Enzymology 8, S. P. Colowick, N. O. Kaplan, p. 584, Acad. Press (1963)]) and the solutions are left in contact for 30 minutes at ambient temperature.

Thereafter, 0.2 ml of a 0.056 M solution of pure ("analytical grade") D(+)-sucrose solution in a 0.1 M sodium maleate buffer of pH=6.0 is added and the mixture is incubated on a water bath at 37° C. for 1 hour. The incubation is stopped by adding 1.6 ml of distilled water and then placing the mixture on a boiling water bath for 2 minutes. The glucose liberated is determined by taking 0.5 ml of the mixture and employing 3 ml of the glucose-oxidase/o-dianisidine-peroxidase reagent.

Colouration develops after 1 hour at 37° C. and the optical density at 420 nm is measured relative to a blank experiment carried out on 0.5 ml of a 0.1 M maleate buffer of pH=6.0.

The optical densities measured at 420 nm are corrected by deduction of the colouration caused by the inhibitor and by the saccharase.

A curve giving the optical density as a function of the concentration of inhibitor in the reaction mixture is then plotted. The concentration of inhibitor which corresponds to an optical density of 50% of that which is obtained in the absence of the inhibitor is termed the 50% inhibitory concentration or $IC_{50}$ (mg/l). For 31,177 RP, it is found that $IC_{50}=16$ mg/l.

The conversion of the $IC_{50}$ to saccharase inhibitor units SIU/mg employs the formul:

$$1000/(IC_{50}\times 0.4\times 200)\ SIU/mg$$

The activity of 31,177 RP is thus 0.8 SIU/mg.

Inhibitory activity on maltase

One maltase inhibitor unit (MIU) is defined as the amount of inhibitor required to inhibit, by 50%, two maltase units. One maltase unit (MU) is the amount of enzyme which in one minute, under the experimental conditions given below produces the scission of one micromole of maltose into 2 micromoles of α-glucose. The α-glucose is determined after mutarotation to β-glucose, by the glucose-oxidase and o-dianisidine-peroxidase system, in accordance with the method described by A. Dahlquist [Methods in Enzymology, 8, S. P. Colowick, N. O. Kaplan, p. 584, Acad. Press (1963)].

In order to carry out the measurement of the anti-maltase activity, 0.14 ml of the inhibitor solution, in a 0.1 M sodium maleate buffer of pH=6.0 (containing 0–40 mg/l of 31,177 RP), is added to 0.06 ml of maltase suspension (0.07 MU/ml of maltase extract from the small intestine of a rat, prepared in accordance with the method described by A. Dahlquist [Methods in Enzymology, 8, S. P. Colowick, N. O. Kaplan, p. 584, Acad. Press (1963)]) and the mixture is kept for 30 minutes at ambient temperature. 0.2 ml of a 0.056 M solution of pure D(+)-maltose solution in a 0.1 M sodium maleate buffer of pH=6.0 is then added and the mixture is incubated on a water bath at 37° C. for 1 hour. The incubation is stopped by adding 1.6 ml of distilled water and then placing the mixture on a boiling water bath for 2 minutes. The glucose liberated is determined by taking 0.5 ml of the mixture and employing 3 ml of the glucose-oxidase/o-dianisidine-peroxidase reagent. Colouration develops after 1 hour at 37° C. and the optical density at 420 nm is measured relative to a blank experiment carried out on 0.5 ml of a 0.1 M maleate buffer of pH=6.0.

The optical densities measured at 420 nm are corrected by deduction of the colouration caused by the inhibitor and by the maltase.

A curve giving the optical density as a function of the concentration of inhibitor in the reaction mixture is then plotted. The concentration of inhibitor which corresponds to an optical density of 50% of that which is obtained in the absence of the inhibitor is termed the 50% inhibitory concentration or $IC_{50}$ (mg/l). For 31,177 RP, it is found that $IC_{50}=2.5$ mg/l.

The conversion of the $IC_{50}$ to maltase inhibitor units MIU/mg employs the formula:

$$(1,000\times 0.004)/(IC_{50}\times 0.4\times 2)\ MIU/mg$$

The activity of 31,177 RP is thus 2 MIU/mg.

The activities determined in vitro have been confirmed in vivo in rats in relation to the hyperglycaemia caused by administration either of wheat starch (2.5 g/kg animal body weight administered orally) or of sucrose (2.5 g/kg animal body weight administered orally). 31,177 RP is administered orally mixed either with starch or with sucrose, and one hour later a blood sample is taken from the abdominal aorta of the rat for the determination of the glycaemia. The hyperglycaemia resulting from the ingestion of starch is reduced by 50% relative to its value in comparison rats, at a dose of 6 mg/kg animal body weight of 31,177 RP administered orally. The hyperglycaemia resulting from the ingestion of sucrose is reduced by 50% relative to its value in comparison rats, at a dose of 25 mg/kg animal body weight of 31,177 RP administered orally.

The acute toxicity of 31,177 RP has been studied principally in mice; the material is atoxic at a dose of 1 g/kg given intravenously.

The organism which produces 31,177 RP is a strain of microorganism which belongs to the genus Streptomyces. It was isolated from a sample of soil, and has been given the number DS 26,320 (NRRL 8141).

This organism, which exhibits characteristics which have not allowed it to be identified with a previously described species, must be considered as a new species and has been given the name *Streptomyces calidus*, DS 26,320.

The isolation of this microorganism was carried out by following the general method which consists of suspending a small amount of soil in sterile distilled water, diluting the suspension to different concentrations and spreading a small volume of each dilution on the surface of Petri dishes containing a nutrient agar medium. After incubation for several days at 26° C., which allows the microorganisms to develop, the colonies which it is desired to isolate in order to continue their study are removed and transplanted onto nutrient agar slopes in order to obtain more abundant cultures thereof. *Streptomyces calidus* DS 26,320 forms oval to cylindrical spores with rounded ends, the spores measuring 1.0 to 1.2μ/0.5 to 0.8μ. It exhibits sporophores in clusters; the chains of spores, which can comprise up to several tens of spores are loose and flexuose and are prone to assume a sinuous shape, or to curl at their end portion so as to form a hook or a very broad coil. According to its mode of sporulation, *Streptomyces calidus* DS 26,320 falls within the *Retinaculum Apertum Section* of the Pridham classification. *Streptomyces calidus* DS 26,320 develops well at 26° C. and at 37° C., a little more moderately, though positively, at 50° C., less well at 52° C. and not at all at 55° C. It exhibits a sporulated aerial mycelium of a yellowish grey, or greyish yellow to grey, colour. On all its culture media, it forms a vegetative mycelium which ranges from more or less deep brown to black-brown, most frequently hidden by the aerial mycelium. It possesses the property of producing melanin pigments on organic media, in particular on the Waksman special tyrosine/yeast extract agar (melanin formation medium), and also of forming soluble pigments of deep brown to black-brown colour on the majority of the synthetic media.

In its cultures, carried out at 26° C., it exhibits the following biochemical characteristics:
production of melanin: positive
production of $H_2S$: positive
tyrosinase: positive
liquefaction of gelatine: positive
utilisation of cellulose: positive
production of nitrites from nitrates: zero on nutrient broth containing nitrates; positive on synthetic media
hydrolysis of starch: positive
culture on skimmed milk: rapid peptonisation without coagulation; moderate alkalinisation of the pH, which changes from 6.3 to 7.3 in 1 month.

The culture characteristics of *Streptomyces calidus* DS 26,320 are summarised in Table II which follows. Unless otherwise stated the characteristics given are of cultures which have reached a good stage of development, i.e. cultures of about 2 to 3 weeks at 26° C. These characteristics were observed on nutrient agars and broths usually employed to determine the morphological characteristics of strains of Streptomyces, the cultures on agar media being carried out on agar slopes. A certain number of the culture media used were prepared in accordance with formulations given in "The Actinomycetes", S. A. Waksman, p. 193-197, Chronica Botanica Company, Waltham, Mass., U.S.A. 1950; in this case, they are indicated by the letter W followed by the number which they are given in "The Actinomycetes". The references or constitutions of the other culture media are as follows:

Ref. A: "Hickey and Tresner's Agar"—T. G. Pridham et coll.—Antibiotics Annual, 1956-1957, p. 950.

Ref. B: "Bennett's Agar"—S. A. Waksman—The Actinomycetes vol. 2, p. 331, No. 30; The William and Wilkins Company, Baltimore 1961.

Ref. C: Formula W-23, with the addition of 2% of agar.

Ref. D: "Yeast Extract Agar"—T. G. Pridham et coll.—Antibiotics Annual, 1956-1957, p. 950.

Ref. E: "Tomato Paste Oatmeal Agar"—T. G. Pridham et coll.—Antibiotics Annual, 1956-1957, p. 950.

Ref. F: "Melanin formation medium"—The Actinomycetes, vol. 2, p. 333, No. 42—S. A. Waksman—The Williams and Wilkins Company, Baltimore, 1961.

Ref. G: W. E. Grundy et coll.—Antibiotics and Chem. 2, 401, 1952.

Ref. H: "Inorganic Salts—Starch Agar"—T. G. Pridham et coll.—Antibiotics Annual, 1956-1957, p. 951.

Ref. I: corresponds to formulation W-1, with 3% of sucrose replaced by 1.5% of glucose.

Ref. J: corresponds to formulation W-1, with 3% of sucrose replaced by 1.5% of glycerol.

Ref. K: corresponds to formulation W-18, with 3% of sucrose replaced by 1.5% of glucose.

Ref. L: corresponds to formulation W-18, with the sucrose omitted and replaced by small strips of filter paper partially immersed in the liquid.

Ref. M: "Manual of Methods for Pure Culture Study of Bacteria" of the Society of American Bacteriologists, Geneva, N.Y. II$_{50}$—18.

Ref. N: "Plain Gelatin"—prepared in accordance with the instructions in the "Manual of Methods for Pure Culture Study of Bacteria" of the Society of American Bacteriologists, Geneva, N.Y., II$_{50}$—18.

Ref. P: skimmed milk in the form of a commercially available powder, reconstituted in accordance with the manufacturer's instructions.

Ref. Q: medium given for investigation of the production of $H_2S$, by: H. D. Tresner and F. Danga—Journal of Bacteriology, 76, 239-244, 1958.

TABLE II

| Culture medium | Degree of development | Vegetative mycelium or underside of the culture | Aerial structure (comprising the combination of the aerial mycelium and the sporulation) | Soluble pigment | Observations and biochemical properties |
|---|---|---|---|---|---|
| Hickey and Tresner agar (Ref. A) | Good | Underside deep brown to black-brown | Greyish white to grey. Medium development | Black-brown | Oval to cylindrical spores with rounded |

TABLE II-continued

| Culture medium | Degree of development | Vegetative mycelium or underside of the culture | Aerial structure (comprising the combination of the aerial mycelium and the sporulation) | Soluble pigment | Observations and biochemical properties |
|---|---|---|---|---|---|
| | | | | | ends, measuring 1.0 to 1.2/0.5 to 0.8 μ. Sporophores in clusters. Flexuose chains of spores which can assume a sinuous shape or curve at their end to form a hook or a very wide coil |
| Bennett agar (Ref. B) | Good | Underside very deep orange-brown | Greyish white to grey. Well developed | Black-brown | |
| Emerson agar (Ref. C) | Good | Underside very deep orange-brown | Light greyish yellow to grey. Medium development | Deep orange-brown | |
| Pridham yeast extract agar (Ref. D) | Good | Underside black | Light yellowish grey to grey. Rather well developed | Black, abundant | |
| Pridham oatmeal and tomato extract agar (Ref. E) | Good | Underside black | Light greyish to grey; numerous droplets of brown-yellow exudation. well developed | Black, abundant | |
| Glucose-peptone agar (W-7) | Moderate | Underside Black-brown | Light yellowish grey to grey. Moderately developed | Black-brown | |
| Nutrient agar (W-5) | Moderate | Underside yellow-brown | Whitish. Poorly developed | Yellow-brown | |
| Tyrosine/yeast extract agar for melanin formation (Ref. F) | Medium | Underside black-brown | Very light greyish. Moderately developed | Black | Production of melanin: positive (readings taken in accordance with the recommendations of the author) |
| Krainsky calcium malate agar (Ref. G) | Moderate | Underside light yellowish brown | Greyish white to grey. Moderately developed | Brownish grey | Solubilisation of the malate: positive, rather good |
| Ovalbumin agar (W-12) | Moderate | Underside deep brown | Light greyish. Moderately developed | Blackish brown | |
| Glucose-asparagine agar (W-2) | Rather good | Underside orange-brown | Light yellowish grey to grey. Rather well developed | Deep orange-brown | |
| Glycerol-asparagine agar (W-3) | Good | Underside very deep orange-brown, ranging to black-brown | Greyish white to grey. Rather well developed | Black-brown | |
| Pridham starch/mineral salts agar (Ref. H) | Good | Underside yellow-brown | Greyish white to grey. Well developed | Rather deep brown-grey | Hydrolysis of starch: positive good. Spores oval to cylindrical with rounded ends, and measuring 1.0 to 1.20/0.5 to 0.8μ. Sporophores in clusters. Chains of flexuose spores which can assume a sinuous shape or can curl at their end end to form a hook or a very wide coil |

TABLE II-continued

| Culture medium | Degree of development | Vegetative mycelium or underside of the culture | Aerial structure (comprising the combination of the aerial mycelium and the sporulation) | Soluble pigment | Observations and biochemical properties |
|---|---|---|---|---|---|
| Starch-nitrate agar (W-10) | Rather good | Underside yellow-brown | Greyish white to grey. Medium development | Yellow-brown | Hydrolysis of starch: positive, moderate |
| Czapek synthetic agar with sucrose (W-1) | Very poor | Underside light brownish yellow | Light greyish. Very poorly developed, almost in the form of traces | Nil | |
| Czapek synthetic agar containing glucose (Ref. I) | Good | Underside black-brown | Light greyish to light yellowish grey. Moderately developed | Black-brown | |
| Czapek synthetic agar containing glycerol (Ref. J) | Good | Underside black-brown | Light greyish to light yellowish grey. Moderately developed | Black-brown | |
| Starch-nitrate broth (W-19) | Good | Thick velum. Underside deep brown | Greyish white. Well developed | Brown | Production of nitrites: positive |
| Czapek glucose broth (Ref. K) | Moderate | Deep brown velum | Nil | Brown | Production of nitrites: positive |
| Czapek cellulose broth (Ref. L) | Very good | Vegetative mycelium deep brown | Light greyish. Abundant on the paper protruding from the broth | Deep brown | Utilisation of cellulose: positive. Production of nitrites: positive |
| Nitrate nutrient broth (Ref. M) | Rather good | Rather thick velum. Underside deep brown | Greyish white. Rather well developed | Deep brown | Production of nitrites: negative |
| Culture on potato (W-27) | Good | Vegetative mycelium thick and wrinkled, deep grey-brown | Greyish white to light greyish yellow. Well developed | Black | Black soluble pigment starting to diffuse into the potato after 24 hours' incubation |
| 12% strength pure gelatine (Ref. N) | Good | Culture well developed at the surface. Underside very deep brown | Greyish white. Moderately developed | Very deep brown | Liquefaction of gelatine: positive, good |
| Skimmed milk (Ref. P) | Good | Yellow-brown ring | Nil | Deep brown | No coagulation. Rapid peptonisation. pH changes from 6.3 to 7.3 in 1 month |
| Tresner and Danga agar (Ref. Q) | Moderate | Blackish brown | Nil | Black | Production of $H_2S$: positive (readings taken in accordance with the recommendations of the author) |

In addition to its peculiarity of developing at 50° C., Streptomyces calidus DS 26,320 exhibits a combination of characteristics which does not coincide exactly with any of those of the strains of Streptomyces previously described and it is for this reason that it must be considered as a new species.

Considering the species which are described in Bergey's Manual of Determinative Bacteriology (7th edition, The Williams and Wilkins Company, Baltimore, 1957) as well as in "The Actinomycetes" (vol. 2, S. A. WAKSMAN, The William and Wilkins Company, Baltimore, 1961), it is to the species Streptomyces phaeochromogenes that it would most easily be possible to compare Streptomyces calidus DS 26,320, which forms melanin pigments on organic media as well as soluble pigments of a brown to black-brown colour on the majority of synthetic media, most frequently develops a brown to black-brown vegetative mycelium on its culture media, gives, in particular on potato, a deep grey-brown vegetative mycelium at the same time as abundant production of a soluble black pigment, and forms a yellowish grey or greyish yellow aerial mycelium, which sometimes becomes brownish yellow-grey in older cultures, to grey. However, it must be differentiated from *S.phaeochromogenes* because, firstly, the latter forms spores which are spherical or in the form of short sticks, and its chains of spores are prone to describe spirals, whilst *S. calidus* DS 26,320 forms spores which are oval to cylindrical with rounded ends but never spherical, and the appearance of its chains of spores corresponds to that of the strains of the *Retinaculum Apertum Series* of Pridham. Furthermore, *S.phaeochromogenes* produces a deep red-brown soluble pigment on nutrient agar, does not form an aerial mycelium on potato and, on a synthetic nitrate agar containing sucrose, shows good development which manifests itself in a brown to almost black vegetative mycelium, and an abundant white aerial mycelium, with a brownish shade, and produces a brown soluble pigment. *S. calidus* DS 26,320, however, produces a yellow-brown soluble pigment on nutrient agar, forms a well developed greyish white to light greyish yellow aerial mycelium on potato and does not produce a soluble pigment on Czapek synthetic nitrate agar containing sucrose, on which medium it only develops very poorly.

The ability of *Streptomyces calidus* DS 26,320 to utilise various sources of carbon or nitrogen to ensure its development was determined in accordance with the principle of the method of Pridham and Gottlieb (J. of Bact. 56, 107–114, 1948). The degree of development was observed on the base medium indicated by the authors, either replacing the glucose by various sources of carbon tested respectively, or replacing the (NH4)2SO4 by the various sources of nitrogen respectively tested. The results are given in Table III.

TABLE III

| Sources of carbon tested | Utilisation | |
|---|---|---|
| D-Ribose | positive | |
| D-Xylose | positive | |
| L-Arabinose | positive | |
| L-Rhamnose | positive, | slow |
| D-Glucose | positive | |
| D-Galactose | positive | |
| D-Fructose | positive | |
| D-Mannose | positive | |
| L-Sorbose | | negative |
| Lactose | positive, | slow |
| Maltose | positive | |
| Sucrose | | negative |
| Trehalose | positive | |
| Cellobiose | positive | |
| Raffinose | | negative |
| Dextrin | positive | |
| Inulin | | negative |
| Starch | positive | |
| Cellulose | positive | |
| Glycogen | positive | |
| Glycerol | positive | |
| Erythritol | | negative |
| Adonitol | | negative |
| Dulcitol | | negative |
| D-Mannitol | positive | |
| D-Sorbitol | | negative |
| Inositol | | negative |
| Salicin | | negative |

| Sources of nitrogen tested | Utilisation | |
|---|---|---|
| NaNO3 | positive | |
| NaNO2 | positive | |
| (NH4)2SO4 | positive | |
| (NH4)2HPO4 | positive | |
| Adenine | positive | |
| Adenosine | positive | |

TABLE III-continued

| | | |
|---|---|---|
| Uracil | | negative |
| Urea | positive | |
| L-Asparagine | positive | |
| Glycine | positive | |
| Sarcosine | | negative |
| DL-Alanine | positive | |
| DL-Valine | positive | |
| DL-Aspartic acid | positive | |
| L-Glutamic acid | positive | |
| L-Arginine | positive | |
| L-Lysine | positive | |
| DL-Threonine | positive | |
| DL-Methionine | | negative |
| Taurine | | negative |
| L-Tyrosine | positive | |
| DL-Proline | positive | |
| L-Histidine | positive | |
| L-Tryptophane | positive | |
| Betaine | | negative |

According to a feature of the invention, the glycopeptide 31,177 RP is produced by aerobically cultivating *Streptomyces calidus* DS 26,320 (NRRL 8141) or a mutant thereof capable of producing the glycopeptide in an aqueous nutrient medium containing assimilable sources of carbon, nitrogen and inorganic substances and isolating from the medium 31,177 RP formed during the culture.

The culture of *Streptomyces calidus* DS 26,320 can be carried out by any of the known aerobic surface or submerged culture methods, but the latter are preferred for reasons of convenience. For this purpose, the various types of apparatus which are currently employed in the fermentation industry may be used.

In particular, the following sequence of operations may be adopted:

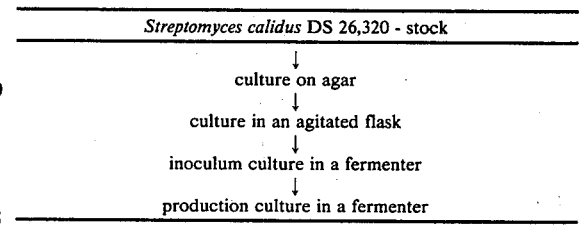

The fermentation medium must contain an assimilable source of carbon and an assimilable source of nitrogen and inorganic substances and, optionally, growth-promoting factors and thickeners; all these ingredients may be supplied as well-defined products or complex mixtures such as those found in biological products of various origins.

As sources of assimilable carbon there may be used carbohydrates such as glucose, invert sugar, lactose, dextrins, starch, cellulose or other carbon-containing substances such as sugar alcohols, e.g. glycerol or mannitol, or certain organic acids, e.g. citric acid, lactic acid and tartaric acid. Certain animal or vegetable oils such as lard oil or soya bean oil may be advantageously used instead of, or in admixture with the aformentioned substances. Glucose and glycerol may be used as particularly advantageous sources of carbon.

The suitable sources of assimilable nitrogen are extremely varied. They may be very simple chemical compounds such as nitrates, inorganic or organic ammonium salts, urea or certain aminoacids. They may also be complex substances containing principally nitrogen in a protein form, e.g. casein, lactalbumin, gluten and their hydrolysates, soya bean flour, peanut meal, fish meal, meat extract, yeast extract, distillers' solubles and corn-steep liquor. The casein hydrolysates may be used as particularly advantageous sources of nitrogen.

Amongst the inorganic substances added, some may have a buffering or neutralising effect, such as the alkali metal or alkaline earth metal phosphates, or the carbonates of calcium or magnesium. Others contribute to the ionic equilibrium necessary for the development of *Streptomyces calidus* DS 26,320 and for the production of 31,177 RP such as the alkali metal and alkaline earth metal chlorides and sulphates. Some of them act more especially as activators of the metabolism of *Streptomyces calidus* DS 26,320, e.g. the salts of iron and of cobalt. The salts of iron or of cobalt may be used as particularly advantageous inorganic salts.

Suitable growth-promoting factors are products of a vitamin nature, e.g. riboflavin, folic acid and pantothenic acid.

The most commonly used thickeners are starch, carboxymethylcellulose and agar.

The pH of the fermentation medium at the start of the culture should preferably be between 6.0 and 7.8, and more preferably between 6.4 and 7.6. The optimum fermentation temperature is 25° to 32° C., but satisfactory production is achieved at temperatures between 23° and 35° C. The rate of aeration of the fermentation medium may vary within quite wide limits, but is has been found that aeration rates of 0.3 to 2 liters of air per liter of medium per minute are particularly suitable. The maximum yield of 31,177 RP is obtained after 23 hours to 5 days culture, but this period depends predominantly on the medium used.

It will be seen from the preceding text that the general conditions for the culture of *Streptomyces calidus* DS 26,320 for the production of 31,177 RP can vary quite widely and can be adapted for each particular requirement.

31,177 RP can be isolated from the fermentation broth in the following manner:

The cells of the microorganism are separated off by centrifuging or by filtration of the medium at a pH which is preferably from 6.0 to 7.0, after which the filtrate obtained is concentrated to a volume of from one-quarter to one-sixth of its initial volume; the concentrate is dialysed against distilled water and a poor solvent for 31,177 RP, such as isopropanol, is added to the cold dialysate to cause the crude product to precipitate.

The crude product thus obtained may be purified by the usual physico-chemical methods, for example:
(i) fractional precipitation from aqueous solutions using poor solvents for 31,177 RP, such as lower alcohols, preferably isopropanol, or water-miscible ketones, preferably acetone;
(ii) dialysis across a membrane, preferably a regenerated cellulose membrane, against water, to remove impurities of low molecular weight and
(iii) chromatography of aqueous solutions of 31,177 RP on various adsorbents such as the aluminas, ion exchangers with basic groups, preferably diethylaminoethyl-cellulose, and macro-crosslinked gels, preferably having a polyamide structure.

In the course of the isolation and purification procedures, the series of determinations necessary to estimate the quantity of 31,177 RP in the products are carried out by an adaptation of the method of G. Noelting and P. Bernfeld, Helv. Chim. Acta 31, 286 (1948) on an automatic apparatus, with the following variations: the incubation temperature used is 30° C., and sugars formed are determined by reduction of ferric ferricyanide.

The titre, expressed in U/mg., is calculated by comparison with the inhibition produced by a partially purified product having a titre of about 1000 IU/mg.

The following Example illustrates the invention.

EXAMPLE 1

(A) Fermentation

The following are introduced into a 170 liter fermenter:
peptone: 1,200 g
yeast extract: 600 g
glucose monohydrate: 1,200 g
agar: 240 g
tap water, sufficient to make up to 110 liters.

The pH is adjusted to 7.3 with 10 N sodium hydroxide solution (70 cc). The mixture is sterilised by bubbling steam at 122° C. through it for 40 minutes. After cooling, the volume of the broth is 120 liters because of the condensation of the steam during the sterilisation, and the pH is 6.65; the broth is inoculated with a culture (200 cc) of *Streptomyces calidus* DS 26,320 prepared in a shaken Erlenmeyer flask. The culture is developed at 30° C. for 23 hours whilst stirring and aerating with sterile air; it is then suitable for inoculating the production culture.

The production culture is carried out in an 800 liter fermenter containing the following:
distiller's solubles: 2 kg
kidney beans kernels: 16 kg
glucose monohydrate: 2 kg
soya bean oil: 4 liters
sodium chloride: 2 kg
magnesium sulphate: 800 g
20 g/l solution of cobalt chloride hexahydrate: 0.4 liter
tap water sufficient to make up to 370 liters.

The beans are precooked for 30 minutes at 122° C. in 300 liters of water and then, after cooling, the other starting materials are added. The pH of the medium is adjusted to 7.5 by adding 10 N sodium hydroxide solution (350 cc), and the broth is then sterilised by bubbling steam at 122° C. through it for 40 minutes. After cooling, the volume of the broth is 400 liters because of the condensation of steam during the sterilisation; the pH of the medium is 6.6; it is inoculated with the inoculum culture (40 liters), produced in the 170 liter fermenter, described above. The culture is developed at 26° C. for 100 hours with agitation using a stirrer rotating at 205 revolutions per minute and aeration with sterile air (20 m³/hour). At the end of the operation, the pH of the culture is 6.3 and the volume of the broth is 420 liters. The enzymatic activity (amylase-inhibiting activity) of the must is 2,700 U/cc.

(B) Extraction

The must (420 liters) prepared as described above, having an enzymatic activity (amylase-inhibiting activity) of 2,700 U/cc, is filtered on a filter press with the aid of a filtration aid (30 kg) to obtain a filtrate (400 liters).

The filtrate obtained (200 liters) is concentrated under reduced pressure at 35° C. to a volume of 40 liters.

The concentrate, the pH of which is adjusted to 6.5 by adding hydrochloric acid (50 cc; 6 N acid) is cooled and then dialysed for 12 hours by circulation in a closed circuit in a plate dialyser equipped with a "Cuprophane" membrane in 1 m² surface area, and fed with distilled water cooled to 4° C.; the final volume of the concentrate is 45 liters. Isopropanol (45 liters) cooled to −10° C. is added to the concentrate. The precipitate which forms is removed by centrifuging and isopropanol (68 liters) cooled to −10° C. is then added to the supernatant liquor; the precipitate obtained is isolated by centrifuging and is taken up in distilled water (4 liters) cooled to 4° C. The pH of the solution is 6.5. This solution is lyophilised to yield 31,177 RP (682 g), having an enzymatic activity of 540 U/mg.

(C) Purification—stage 1

The product (500 g; enzymatic activity 540 U/mg), precipitated by isopropanol as described above, is dissolved in distilled water (10 liters). The solution obtained is clarified by filtration and then passed through a column of 15 cm diameter containing a height of 60 cm of alumina, at pH=4 adjusted by means of hydrochloric acid, in water (about 5 liters) as the solvent. When the solution has passed through, elution is continued with distilled water (about 11 liters).

Figure 2:
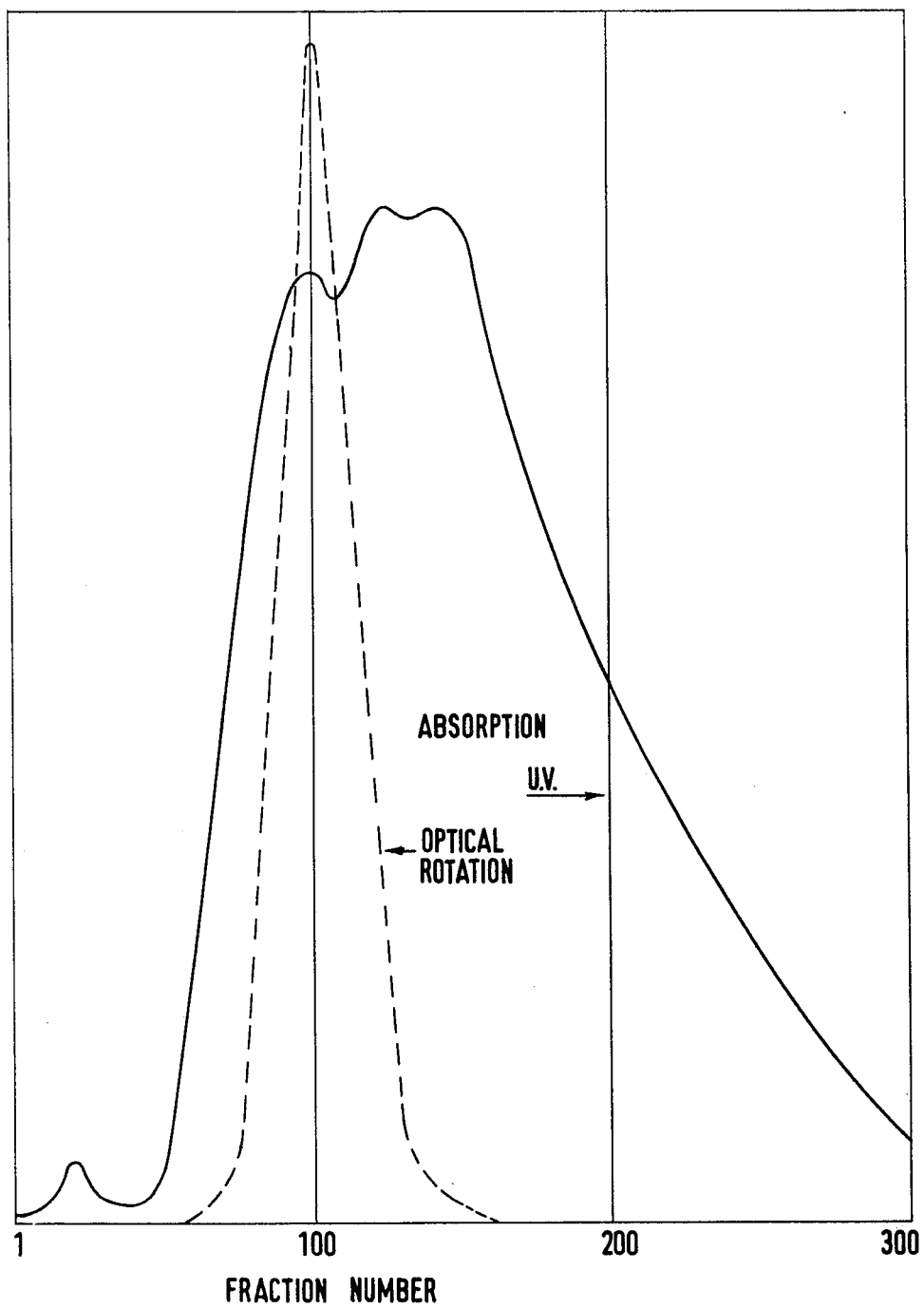

The speed of elution is regulated by means of a pump to 500 cc/hour and the optical density of the eluate is measured at 254 nm by means of a continuous analyser. The eluate is collected in fractions of 60 cc and the optical rotation, for the D line of sodium, of the fractions which absorb at 254 nm is measured. FIG. 2 represents, in relative values, the UV absorption and the optical rotation of the eluate fractions. The fractions which contain the product which rotates the plane of polarised light are collected (total volume about 3.5 liters), concentrated and then lyophilised. A product (101.2 g) containing 1,350 U/mg is thus obtained.

(D) Purification—stage 2

The product (64 g) obtained as described above, and containing 1,350 U/mg, is dissolved in distilled water (320 cc), and isopropanol (960 cc) and Whatman cellulose, type CF₁ (about 100 g) are then added.

Figure 3:
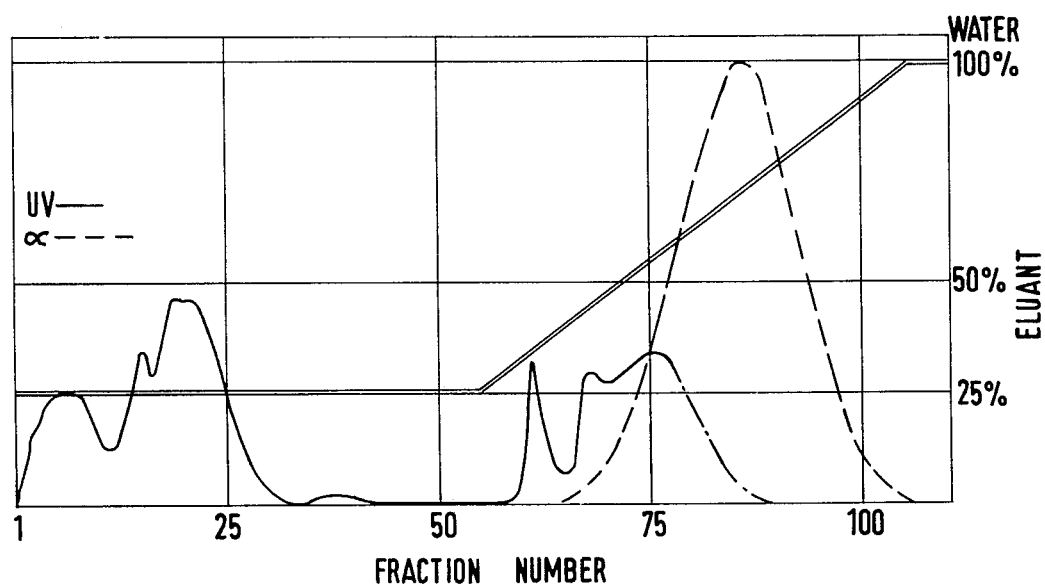

The paste thus obtained is placed, as a uniform layer, at the top of a column of 15 cm diameter, containing Whatman CF₁ cellulose (5.5 kg) in a mixture of isopropanol and water (3:1, v/v). The height of the column of cellulose is 110 cm and the thickness of the cellulose charged with product is about 5 cm. Elution is carried out with a solvent mixture (isopropanol:water=3:1, v/v; 27.5 liters) at a flow rate of 1.2 l/hour, after which the proportion of water in the mixture is increased linearly until elution is with water alone, at the same flow rate (total volume of eluate obtained with the composition gradient=25 liters). The eluate is collected in fractions of about 500 cc and the optical density of the fractions is measured continuously by a Seive Eliograph analyser at 280 nm. The optical rotation of the fractions at the D line of sodium, is also measured particularly for the fractions eluted with the composition gradient. The diagram in FIG. 3, which represents the U.V. absorption at 280 nm as a function of the number of the fractions, exhibits several peaks. The fractions corresponding to these peaks, which originate from the elution with the mixture of isopropanol and water (3:1, v/v) and at the start of the composition gradient, do not exhibit optical rotation. The fractions which alter the plane of polarised light are obtained after elution by the end of the composition gradient; they still contain fractions which absorb at 280 nm.

The fractions corresponding to the peak which rotate the plane of polarised light are combined (fractions 65 to 105, amounting to 19.6 liters). The isopropanol is removed by evaporation under reduced pressure (2 mm Hg) and the product is then lyophilised. A product (29 g) containing 2,950 U/mg is thus obtained.

(E) Purification—stage 3

The product (67.3 g) originating from three operations similar to that described above are dissolved in distilled water (1,350 cc). The solution obtained is placed at the top of a chromatography column of 15 cm diameter containing a height of 110 cm of diethylaminoethyl-cellulose (ion exchanger:DEAE cellulose Whatman, type DE 11, about 5 kg).

Before use, the ion exchanger is washed with 0.5 N hydrochloric acid (10 l/kg of ion exchanger), with water, with 0.5 N sodium hydroxide solution (10 l/kg of ion exchanger) and with water, and is finally equilibrated in a buffer containing tris-(hydroxymethyl)-aminomethane (3.025 g per liter) and adjusted to pH=8.0 by means of 1 N hydrochloric acid (26-27 cc).

The column is eluted with the same buffer (32 liters) at a flow rate of 1.2 l/hour. The eluate is collected in fractions of about 320 cc and their absorption is measured continuously by means of an L.K.B. Uvicord type I analyser at 254 nm to detect protein impurities. The optical rotations of the fractions for the D line of sodium are also measured.

Figure 4:
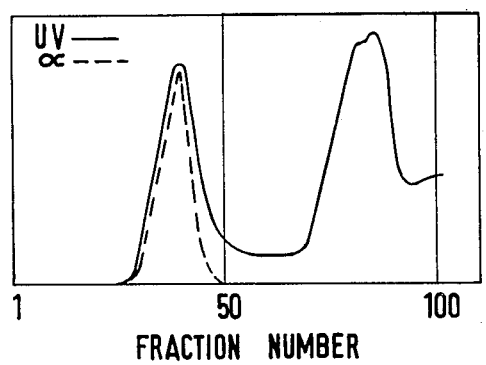

The diagram in FIG. 4, which gives the U.V. absorption at 254 nm as a function of the number of the fractions, exhibits two peaks. Fractions 35 to 50 (total volume 4.8 liters), which correspond to the first of these peaks, exhibit a noteworthy optical rotation for the D line of sodium. Fractions 35 to 50 are combined, concentrated to one-tenth of their volume and dialysed at +4° C. against water (3×50 liters). The dialysate is lyophilised. A pure product (15.85 g) containing 9.430 IU/mg is thus obtained.

The present invention includes within its scope pharmaceutical compositions comprising 31,177 RP, and optionally another hypoglycaemic or antidiabetic agent, in association with one or more pharmaceutically acceptable carriers or diluents. These compositions have hypoglycaemic properties and are particularly useful for combating obesity, diabetes, prediabetes and atherosclerosis. The invention includes especially such compositions made up for oral administration.

Solid compositions for oral administration include tablets, pills, powders or granules. In such solid compositions, the 31,177 RP according to the invention is mixed with one or more inert diluents such as sucrose, lactose or starch. The solid compositions may also comprise additional substances other than inert diluents, for example lubricating agents such as magnesium stearate.

Liquid compositions for oral administration include pharmaceutically-acceptable emulsions, solutions, suspensions, syrups and elixirs containing inert diluents such as water or liquid paraffin. These liquid compositions may also contain substances other than inert diluents, for example wetting agents, sweeteners or flavourings.

31,177 RP may also be used in the foodstuff industry, in foodstuffs containing starch, to prevent possible decomposition, and secondly in dietetics, in foodstuffs intended for subjects suffering from obesity. The foodstuffs will generally contain from 0.15 to 1% (w/w) of 31,177 RP based on the contained starch.

In general, the physician will decide the most suitable posology taking into account the age, weight and other factors relating to the subject to be treated. Generally, a satisfactory dosage is 20 to 200 mg. per day of 31,177 RP, administered orally, in the case of an adult.

The following Example illustrates compositions according to the invention.

EXAMPLE 2

Granules having the following composition are prepared in accordance with the usual technique:

31,177 RP: 0.060 g.
corn starch: 0.060 g.
mannitol: 0.074 g.
polyvinylpyrrolidone: 0.006 g.

We claim:

1. The glycopeptide herein designated 31,177 RP, which has the following characteristics: it is soluble in water to the extent of more than 1,000 g/l; its solubility decreases rapidly in aqueous-alcoholic and aqueous-acetone mixtures and drops to less than 0.1 g/l in anhydrous alcohols, acetone, hexane, ethyl acetate, diethyl ether and chlorinated solvents;

analysis of the products of acid hydrolysis shows principally lysine and glucose;

it contains carbon, hydrogen, oxygen, nitrogen and sulphur, the relative proportions being approximately: C=46.2% H=6.05% O=46.11% N=1.44% S=0.20%;

its molecular weight is between 10,000 and 20,000;

its optical rotation (c=0.4, water) is:

$[\alpha]_D^{20} = +149.5° \pm 2.5°$
$[\alpha]_{436}^{20} = +295° \pm 4.0°$
$[\alpha]_{365}^{20} = +448° \pm 5.5°$ it does not exhibit a characteristic absorption in the ultraviolet spectrum between 220 and 400 nm; and its infra-red spectrum (determined on tablets of a mixture with KBr) shows principal absorption bands as follows:

3470 shoulder, 3400 shoulder, 3350 very strong, 3270 shoulder, 3100 shoulder, 3050 shoulder, 3000 shoulder, 2980 shoulder, 2930 strong, 2900 shoulder, 2830 shoulder, 2780 shoulder, 2540 shoulder, 2350 very weak, 2100 very weak, 1985 very weak, 1945 very weak, 1900 very weak, 1850 very weak, 1760 very weak, 1630 medium, 1450 shoulder, 1410 strong, 1370 weak, 1335 shoulder, 1305 shoulder, 1240 weak, 1160 strong, 1100 shoulder, 1075 shoulder, 1030 very strong, 935 shoulder, 920 medium, 850 medium, 785 shoulder, 770 shoulder, 760 medium, 720 shoulder, 700 medium, 640 shoulder, 610 shoulder, 580 medium, 525 weak, 440 shoulder, 410 shoulder and 370 shoulder $cm^{-1}$.

2. Process for the production of the glycopeptide 31,177 RP claimed in claim 1, which comprises aerobically cultivating *Streptomyces calidus* DS 26,320 (NRRL 8141) or a mutant thereof capable of producing the glycopeptide, in an aqueous nutrient medium containing assimilable sources of carbon, nitrogen and inorganic substances, and isolating from the medium 31,177 RP formed during the culture.

3. Process according to claim 2 in which the culture is effected under submerged aerobic conditions commencing at a pH between 6.0 and 7.8 and a temperature from 23° to 35° C.

4. Process according to claim 3 in which the pH of the culture medium at the start of the culture is between 6.4 and 7.6.

5. Process according to claim 3 in which the temperature of the culture medium is 25° to 32° C.

6. Process according to claim 2 in which the culture medium is aerated at a rate of 0.3 to 2 liters of air per liter of medium per minute.

7. Process according to claim 2 in which the culture is continued for 23 hours to 5 days.

8. Process according to claim 2 in which 31,177 RP is isolated from the culture medium by separating off the cells of the microorganism by centrifuging or by filtration of the medium at a pH from 6.0 to 7.0, concentrating the filtrate obtained to a volume of from one quarter to one sixth of its initial volume, dialysing the concentrate against distilled water and adding to the cold dialysate a poor solvent for 31,177 RP to cause the crude product to precipitate.

9. Process according to claim 8 in which the poor solvent for 31,177 RP is isopropanol.

10. Process according to claim 8 in which the crude product obtained is purified by fractional precipitation from aqueous solutions using poor solvents for 31,177 RP, dialysis across a membrane against water or by chromatography of aqueous solutions of 31,177 RP.

11. A biologically pure culture of *Streptomyces calidus* DS 26,320 having the identifying characteristics of NRRL 8141, said culture being capable of producing the glycopeptide 31,177 RP in a recoverable quantity upon fermentation in an aqueous nutrient medium containing assimilable sources of carbon, nitrogen and inorganic substances.

* * * * *